United States Patent [19]
Weinshank et al.

[11] Patent Number: 5,595,880
[45] Date of Patent: Jan. 21, 1997

[54] DNA ENCODING AN $\alpha_{2B}$ ADRENERGIC RECEPTOR AND USES THEREOF

[75] Inventors: Richard L. Weinshank, New York, N.Y.; Paul R. Hartig, Mahwah, N.J.

[73] Assignee: Synaptic Pharmaceutical Corporation, Paramus, N.J.

[21] Appl. No.: 965,040

[22] Filed: Oct. 22, 1992

Related U.S. Application Data

[60] Continuation of Ser. No. 707,604, May 30, 1991, abandoned, which is a division of Ser. No. 428,856, Oct. 30, 1989, Pat. No. 5,053,337.

[51] Int. Cl.$^6$ .............................. C12Q 1/00; C12Q 1/68
[52] U.S. Cl. .............................. 435/7.21; 435/6; 435/7.1
[58] Field of Search .............................. 435/6, 7.1, 7.21; 530/350; 536/24.31

[56] References Cited

PUBLICATIONS

Bacchetti, S. et al. Transfer of the gene for thymidine kinase to thymidine kinase–deficient human cells by . . . Proc. Natl. Acad. Sci. USA. (Apr. 1977) 74:1590–1594.

Regan, J. W. et al. Cloning and expression of a human kidney cDNA for an $\alpha_2$–adrenergic receptor subtype. Proc. Natl. Acad. Sci. USA. (Sep. 1988) 85:6301–6305.

Fraser et al. Biosis Abstract No. 85029825 J Biol Chem 262 (31) 1987. 14843–14846.

Kobilka et al. Embase Abstract No. 87225795 Science (USA) 1987, 238/4827, 650–656.

Regan et al. Biosis Abstract No. 86124412 Proc Natl Acad Sci USA 85(17) 1988. 6301–6305.

*Primary Examiner*—Margaret Parr
*Assistant Examiner*—David Schreiber
*Attorney, Agent, or Firm*—John P. White

[57] ABSTRACT

The present invention provides an isolated nucleic acid molecule encoding an $\alpha_{2B}$-adrenergic receptor, and an isolated protein which is a human $\alpha_{2B}$-adrenergic receptor. The invention also provides vectors comprising DNA molecules encoding a human $\alpha_{2B}$-adrenergic receptor, and vectors adapted for expression of the $\alpha 2b_{2B}$-adrenergic receptor in bacterial, yeast, or mammalian cells. In addition, the invention provides a DNA probe useful for detecting nucleic acid encoding the $\alpha 2b_{2B}$-adrenergic receptor, a method for determining whether a ligand which is not known to be capable of binding to the $\alpha 2b_{2B}$-adrenergic receptor can bind to the $\alpha_{2B}$-adrenergic receptor on the surface of a cell, and a method of screening drugs to identify drugs to identify drugs which specifically interact with, and bind to, the $\alpha_{2B}$-adrenergic receptor. The invention herein also concern an antibody directed to the human $\alpha_{2B}$-adrenergic receptor, such as a monoclonal antibody directed to an epitope of the $\alpha_{2B}$-adrenergic receptor present on the surface of a cell and having an amino acid sequence included within the amino acid sequence shown in FIG. 2.

5 Claims, 9 Drawing Sheets

FIGURE 2A

```
        -280                    -260                    -240
CTGCAGGCGCGGCTGGGGCGAAACGTGCGAGCTGAGCGGGCGCAAGGTCCTCCGCGCCTC

-220                    -200                    -180
CTTTAAGAACCGGCCCAGCCCGGCCCGGCGCCCCAGAGCGTACGGCATCCGCGTGGCGGA

-160                    -140                    -120
GGGCGCGACTTTCTCCGGTGCCGGGCGGGACGGGGACGGCGGGCGGGACAACTTGGGAAA

-100                     -80                     -60
CTTCTCTGGGGCGGACGGCAGGGACCCCGGGCACCGTGGAGGAGGATGTAGGAGGGCGGC

-40                     -20                      0
TCTGGTCCTGGGTGTTCCCGACCTCCTAGGCCCCGCTCGTCCAGGCCATGGGGTCCAGCG
                                                  M  G  S  S  A
          20                      40                     60
CCTCGGGCCGGAGGGGGAGCTCTTGTCTAGCCGAGCCGGGAGGTGTGTCACGGTGCACTG
  S  G  R  R  G  S  S  C  L  A  E  P  G  G  V  S  R  C  T  G 80                     100                    120
GGCGGGCAGCGCTCCCTCTGCCCACCTCCCGCCCCGTCATGGACCACCAGGACCCCTACT
  R  A  A  L  P  L  P  T  S  R  P  V  M  D  H  Q  D  P  Y  S
```

FIGURE 2B

```
           140                      160                      180
CCGTGCAGGCCACAGCGGCCATAGCGGCGGCCATCACCTTCCTCATTCTCTTTACCATCT
  V   Q   A   T   A   A   I   A   A   A   I   T   F   L   I   L   F   T   I   F 200                      220                      240
TCGGCAACGCTCTGGTCATCCTGGCTGTGTTGACCAGCCGCTCCTGGCGCGCCCCTCAGA
    G   N   A   L   V   I   L   A   V   L   T   S   R   S   W   R   A   P   Q   N 260                      280                      300
ACCTGTTCCTGGTGTCGCTGGCCGCCGCCGACATCCTGGTGGCCACGCTCATCATCCCTT
  L   F   L   V   S   L   A   A   A   D   I   L   V   A   T   L   I   I   P   C 320                      340                      360
GCTCGCTGGCCAACGAGCTGCTGGGCTACTGGTACTTCCGGCGCACGTGGTGGCAGGTGT
    S   L   A   N   E   L   L   G   Y   W   Y   F   R   R   T   W   W   Q   V   Y 380                      400                      420
ACCTGGCGCTCGACGTGCTCTTCTGCACCTCGTCCATCGTGCACCTGTGCGCCATCAGCC
    L   A   L   D   V   L   F   C   T   S   S   I   V   H   L   C   A   I   S   L 440                      460                      480
TGGACCGCTACTGGGCCGTGAGCCGCGCGCTGGAGTACAACTCCAAGCGCCACCCCGCCC
  D   R   Y   W   A   V   S   R   A   L   E   Y   N   S   K   R   H   P   A   R 500                      520                      540
GCATCAAGTGCATCATCCTCACTGTGTGGCTCATCGCCGCCGTCATCTCGCTGCCGCCCC
  I   K   C   I   I   L   T   V   W   L   I   A   A   V   I   S   L   P   P   L 560                      580                      600
TCATCTACAAGGGCGACCAGGGCCCCCAGCCGCGCGGGCGCCCCCAGTGCAAGCTCAACC
  I   Y   K   G   D   Q   G   P   Q   P   R   G   R   P   Q   C   K   L   N   Q
```

FIGURE 2C

```
           620                   640                    660
AGGAGGCCTGGTACATCCTGGCCTCCAGCATCGGATCTTTCTTTGCTCCTTGCCTCATCA
   E   A   W   Y   I   L   A   S   S   I   G   S   F   F   A   P   C   L   I   M 680                   700                    720
TGATCCTTGTCTACCTGCGCATCTACCTGATCGCCAAACGCAGCAACCGCAGAGGTCCCA
   I   L   V   Y   L   R   I   Y   L   I   A   K   R   S   N   R   R   G   P   R 740                   760                    780
GGGCCAAGGGGGGGCCTGGGCAGGGTGAGTCCAAGCAGCCCCGACCCGACCATGGTGGGG
   A   K   G   G   P   G   Q   G   E   S   K   Q   P   R   P   D   H   G   G   A 800                   820                    840
CTTTGGCCTCAGCCAAACTGCCAGCCCTGGCCTCTGTGGCTTCTGCCAGAGAGGTCAACG
   L   A   S   A   K   L   P   A   L   A   S   V   A   S   A   R   E   V   N   G 860                   880                    900
GACACTCGAAGTCCACTGGGGAGAAGGAGGAGGGGGAGACCCCTGAAGATACTGGGACCC
   H   S   K   S   T   G   E   K   E   E   G   E   T   P   E   D   T   G   T   R 920                   940                    960
GGGCCTTGCCACCCAGTTGGGCTGCCCTTCCCAACTCAGGCCAGGGCCAGAAGGAGGGTG
   A   L   P   P   S   W   A   A   L   P   N   S   G   Q   G   Q   K   E   G   V 980                   1000                   1020
TTTGTGGGGCATCTCCAGAGGATGAAGCTGAAGAGGAGGAAGAGGAGGAGGAGGAGGAGG
   C   G   A   S   P   E   D   E   A   E   E   E   E   E   E   E   E   E   E 1040                  1060                   1080
AAGAGTGTGAACCCCAGGCAGTGCCAGTGTCTCCGGCCTCAGCTTGCAGCCCCCCGCTGC
   E   C   E   P   Q   A   V   P   V   S   P   A   S   A   C   S   P   P   L   Q
```

FIGURE 2D

```
        1100              1120              1140
AGCAGCCACAGGGCTCCCGGGTGCTGGCCACCCTACGTGGCCAGGTGCTCCTGGGCAGGG
  Q   P   Q   G   S   R   V   L   A   T   L   R   G   Q   V   L   L   G   R   G 1160              1180              1200
GCGTGGGTGCTATAGGTGGGCAGTGGTGGCGTCGACGGGCGCACGTGACCCGGGAGAAGC
  V   G   A   I   G   G   Q   W   R   R   R   A   H   V   T   R   E   K   R 1220              1240              1260
GCTTCACCTTCGTGCTGGCTGTGGTCATTGGCGTTTTTGTGCTCTGCTGGTTCCCCTTCT
  F   T   F   V   L   A   V   V   I   G   V   F   V   L   C   W   F   P   F 1280              1300              1320
TCTTCAGCTACAGCCTGGGCGCCATCTGCCCGAAGCACTGCAAGGTGCCCCATGGCCTCT
  F   S   Y   S   L   G   A   I   C   P   K   H   C   K   V   P   H   G   L   F 1340              1360              1380
TCCAGTTCTTCTTCTGGATCGGCTACTGCAACAGCTCACTGAACCCTGTTATCTACACCA
  Q   F   F   F   W   I   G   Y   C   N   S   S   L   N   P   V   I   Y   T   I 1400              1420              1440
TCTTCAACCAGGACTTCCGCCGTGCCTTCCGGAGGATCCTGTGCCGCCCGTGGACCCAGA
  F   N   Q   D   F   R   R   A   F   R   R   I   L   C   R   P   W   T   Q   T 1460              1480              1500
CGGCCTGGTGAGCCCGCCTGCGCTGCCCCTGTGGTTGGTGCGGTGGCGCCGGGGTCACCC
  A   W   *

1520              1540              1560
TGCTTCTTGCCCTGCTGTGTGTGGCTAGCCTCCCCTGGGCTTTCTGCTCCCTGCCCAGAT
```

FIGURE 2E

```
         1580                1600                1620
CCTGTAGGCCTCATCTTAGGAACCCCTTGGAGGGGTGGGCAGGGGGCTGCTAGCAAGGG 1640                1660                1680
TCCCAGTGAAGCTTCCCCTTGCCGGCTTAGCTGTGGGGGACCCCTTCTCCACCCTCTCCC 1700                1720                1740
TGAGCACAGGCCGATGGAGGTGGTTCAAATCTCTGGAACATAGCCAAGACCAGGAGAAGA

1760
GAGAGCACTTCTTCCAGAGCCCATC
```

FIGURE 3A

```
Ngcalpha2.Frg   ..MGSSASGR RGSSCLAEPG GVSRCTGRAA LPLPTSRPVM DHQDPYSVQA   48
Alpha2c4.Frg    MASPALAAAL AVAAAAGPNA SGAGERGSGG VANASGASWG PPRGQYSAGA   50
Alpha2c10.Frg   .........  ........MG SLQPDAGNAS WNGTEAPGGG ARATPYSLQV   32
Template.Frg    .........  .........  .........  .........  .........

Ngcalpha2.Frg   TAAIAAAITF LILFTIFGNA LVILAVLTSR SWRAPQNLFL VSLAAADILV   98
Alpha2c4.Frg    VAGLAAVVGF LIVFTVVGNV LVVIAVLTSR ALRAPQNLFL VSLASADILV  100
Alpha2c10.Frg   TLTLVCLACL LMLLTVFGNV LVIIAVFTSR ALKAPQNLFL VSLASADILV   82
Template.Frg    ..*******  *****..I.. .........  ........** *********.

Ngcalpha2.Frg   ATLIIPCSLA NELLGYWYFR RTWWQVYLAL DVLFCTSSIV HLCAISLDRY  148
Alpha2c4.Frg    ATLVMPFSLA NELMAYWYFG QVWCGVYLAL DVLFCTSSIV HLCAISLDRY  150
Alpha2c10.Frg   ATLVIPFSLA NEVMGYWYFG KTWCEIYLAL DVLFCTSSIV HLCAISLDRY  132
Template.Frg    .II..*****  *****....  .........  ....III..  **********

Ngcalpha2.Frg   WAVSRALEYN SKRHPARIKC IILTWLIAA VISLPPLIYK GDQGPQPRGR  198
Alpha2c4.Frg    WSVTQAVEYN LKRTPRRVKA TIVAVWLISA VISFPPLVSL YRQPDGAAY.  199
Alpha2c10.Frg   WSITQAIEYN LKRTPRRIKA IIITCWVISA VISFPPLISI EKKGGGG.G.  180
Template.Frg    .........  .........  ****......IV ********  ***......

Ngcalpha2.Frg   PQ.....CKL NQEAWYILAS S.IGSFFAPC LIMILVYLRI YLIAKRSNRR  242
Alpha2c4.Frg    PQ.....CGL NDETWYIL.S SCIGSFFAPC LIMGLVYARI YRVAKRRTRT  243
Alpha2c10.Frg   PQPAEPRCEI NDQKWYVI.S SCIGSFFAPC LIMILVYVRI YQIAKRRTRV  229
Template.Frg    ..........  *********  *..V..**** *********.  .........
```

FIGURE 3B

```
Ngcalpha2.Frg  GPRAKGGPGQ GESKQPRPDH GGALASAKLP ALASVASARE VNGHSKSTGE 292
Alpha2c4.Frg   LSEKRAPVGP DGASPTTENG LGAAAGEART GTARPRPPTW SRTRAAQRPR 293
Alpha2c10.Frg  PPSRRGPDAV AAPPGGTERR PNGLGPERSA GPGGAEAEPL PTQLNGAPGE 279
Template.Frg   .......... .......... .......... .......... ..........

Ngcalpha2.Frg  KEEGETPEDT GTRALPPSWA ALPNSGQGQK EGVCGASPED EAEEEEEEE  342
Alpha2c4.Frg   GGAPGPLRRG GRRRAGAEGG AGGADGQGAG PGAAQSGALT ASRSPGPGGR 343
Alpha2c10.Frg  PAPAGPRDTD ALDLEESSSS DHAERPPGPR RPERGPRGKG KARASQVKPG 329
Template.Frg   .......... .......... .......... .......... ..........

Ngcalpha2.Frg  EEEECEPQAV PVSPASACSP PLQQPQGSRV LATLRGQVLL GRGVGAIGGQ 392
Alpha2c4.Frg   LSRASSRSVE FFLSRRRRAR SSVC...... .......... .......... 367
Alpha2c10.Frg  DSLRGAGRGR RGSGRRLQGR GRSASGLP.. .......R.. .......... 358
Template.Frg   .......... .......... .......... .......... ..........

Ngcalpha2.Frg  WWRRRAHVTR EKRFTFVLAV VIGVFVLCWF PFFFSYSLGA I.CPKHCKVP 441
Alpha2c4.Frg   ..RRKVAQAR EKRFTFVLAV VMGVFVLCWF PFFFIYSLYG I.CREACQVP 414
Alpha2c10.Frg  RRAGAGGQNL EKRFTFVLAV VIGVFVVCWF PFFFTYTLTA VGCS.....VP 404
Template.Frg   .......... ......**** ****...*** **........ **........

Ngcalpha2.Frg  HGLFQFFFWI GYCNSSLNPV IYTIFNQDFR RAFRRILCRP WTQTAW*... 487
Alpha2c4.Frg   GPLFKFFFWI GYCNSSLNPV IYTVFNQDFR PSFKHILFRR RRRGFRQ*.. 461
Alpha2c10.Frg  RTLFKFFFWF GYCNSSLNPV IYTIFNHDFR RAFKKILCRG DRKRIV*... 450
Template.Frg   ********** ..VII..*** *******... .......... ..........
```

DNA ENCODING AN $\alpha_{2B}$ ADRENERGIC RECEPTOR AND USES THEREOF

This application is a continuation of U.S. Ser. No. 707,604 filed May 30, 1991, now abandoned, which is a divisional of U.S. Ser. No. 428,856 filed Oct. 30, 1989, now U.S. Pat. No. 5,053,337, issued Oct. 1, 1991, the contents of each of which are hereby incorporated by reference into the subject application.

BACKGROUND OF THE INVENTION

Pharmacological studies, and more recently gene cloning, have established that multiple receptor subtypes exist for most, if not all, neurotransmitters. The existence of multiple receptor subtypes provides one mechanism by which a single neurotransmitter can elicit distinct cellular responses. The variation in cellular response can be achieved by the association of individual receptor subtypes with different G proteins and different signalling systems. Further flexibility is provided by the ability of distinct receptors for the same ligand to activate or inhibit the same second messenger system.

Individual receptor subtypes reveal characteristic differences in their abilities to bind a number of ligands, but the structural basis for the distinct ligand-binding properties is not known. Physiologists and pharmacologists have attempted to specify particular biological functions or anatomical locations for some receptor subtypes, but this has met with limited success. Similarly, the biochemical mechanisms by which these receptors transduce signals across the cell surface have been difficult to ascertain without having well-defined cell populations which express exclusively one receptor subtype.

Receptors for epinephrine (adrenaline) are termed adrenergic receptors. The $\alpha_2$-adrenergic receptor belongs to the family of rhodopsin-like signal transducers which are distinguished by their seven-transmembrane configuration and their functional linkage to G-proteins. While all the receptors of the adrenergic type are recognized by epinephrine, they are pharmacologically distinct and are encoded by separate genes. These receptors, known as subtypes, are generally coupled to different second messenger pathways that are linked through guanine-nucleotide regulatory (G) proteins. Among the adrenergic receptors, $\beta_1$ and $\beta2$ receptors activate adenylate cyclase, $\alpha_2$ receptors inhibit adenylate cyclase and $\alpha_1$ receptors activate phospholipase C pathways, stimulating breakdown of polyphosphoinositides (Chung, F. -Z., et al., J. Biol. Chem. 263:4052 (1988); Strader, C. D., et al., Proc. et al. Acad. Sci. USA 84:4384 (1987)).

Radioligand filtration binding techniques have been employed to characterize the adrenergic receptor family (Timmermans, P. B. M. W. M., "α Adrenoceptors", in *Receptor Pharmacology and Function,* Williams, M., Glennon R., and Timmermans, P. (eds.) 1989; Dekker, N.Y. pp. 173–205; Byland, D. B. TIPS 9:356 (1988)). Using these methods, two major classes of α-adrenoceptors have been described, $\alpha_1$ and $\alpha_2$. These differ in their selectivity for drugs. $\alpha_1$ receptors can be labeled selectively with $^3$H-WB4101 or $^3$H-Prazosin. $\alpha_2$ receptors can be labeled selectively with $^3$H-Yohimbine and $^3$H-Rauwolscine. Within the $\alpha_2$ population, at least 3 subtypes have been defined, again on the basis of drug selectivity. All display high affinity for $^3$H-Yohimbine or $^3$H-Rauwolscine but differ in their susceptibility to competition by drugs. The $\alpha_{2A}$ subtype is very sensitive (nM) to competition by oxymetazoline. The $\alpha_{2B}$ subtype is sensitive to competition by Prazosin. The $\alpha_{2C}$ subtype is pharmacologically similar to the $\alpha_{2B}$ but $\alpha_{2C}$ has a higher (10 fold) affinity for $^3$H-Rauwolscine relative to that of the $\alpha_{2B}$ subtype. Applicants have cloned a human, $\alpha_{2B}$-adrenergic receptor, NGC-$\alpha_{2B}$, which has been transfected into a heterologous expression system, producing a membrane protein with binding properties consistent with its preliminary characterization as an $\alpha_2$ receptor subtype. The results from binding studies are consistent with the projected subtype based on amino acid sequence homology.

A variety of structural features which are invariant in the family of neurotransmitter molecules were present in clone NGC-$\alpha_{2B}$. The greatest homology was found between clone NGC-$\alpha_{2B}$ and the human platelet $\alpha_2$ and the human kidney $\alpha_2$-adrenergic receptors. (B. K. Kobilka, et al., Science 238:650–656, 1987; J. W. Regan, et al., Proc. Natl. Acad. Sci. (USA) 85: 6301–6305, 1988). In both cases, an overall homology of approximately 45% was observed, while the homology within the transmembrane regions alone was approximately 75%.

The receptor encoded by clone NGC-$\alpha_{2B}$ shares numerous sequence and structural properties with the family of receptor molecules that has been predicted to span the lipid bilayer seven times. This family includes rhodopsin and related opsins (Nathans, J. and Hogness, D. S., Cell 34:807 (1983)), the α and β adrenergic receptors (Dohlman, H. G., et al., Biochemistry 26:2657 (1987)), the muscarinic cholinergic receptors (Bonner, T. I., et al., Science 237:527 (1987)), the substance K neuropeptide receptor, (Masu, Y., et al., Nature 329:836 (1987)), the yeast mating factor receptors, (Burkholder, A. C. and Hartwell, L. H., Nucl. Acids Res. 13:8463(1985); Hagan, D. C., et al., Proc. Natl. Acad. Sci. USA 83:1418 (1986)); Nakayama, N. et al., EMBO J. 4:2643 (1985)), the serotonin receptor, and the oncogene c-mas, (Young, et al., Cell 45:711 (1986)). Each of these receptors is thought to transduce extracellular signals by interaction with guanine nucleotide-binding (G) proteins (Dohlman, H. G., et al., Biochemistry 26:2657 (1987); Dohlman, H. G., et al., Biochemistry 27:1813 (1988); O'Dowd, B. F., et al., Ann. Rev. Neurosci., in press).

SUMMARY OF THE INVENTION

The present invention provides an isolated nucleic acid molecule encoding a human $\alpha_{2B}$-adrenergic receptor.

This invention also provides an isolated protein which is a human $\alpha_{2B}$-adrenergic receptor.

The invention also provides vectors comprising DNA molecules encoding a human $\alpha_{2B}$-adrenergic receptor, for example a plasmid comprising the DNA encoding the $\alpha_{2B}$-adrenergic receptor designated pNGC-$\alpha_{2B}$ and deposited under ATCC Accession No. 68144.

Additionally, the present invention provides vectors adapted for expression in bacterial, yeast, or mammalian cells which comprise a DNA molecule encoding the $\alpha_{2B}$-adrenergic receptor and the regulatory elements necessary for expression of the DNA in the cell.

The present invention further provides the transfected Ltk⁻ cell designated L-NGC-$\alpha_{2B}$ and deposited under ATCC Accession No. CRL 10275.

In addition, the invention provides a DNA probe useful for detecting nucleic acid encoding the $\alpha_{2B}$-adrenergic receptor comprising a nucleic acid molecule of at least about 15 nucleotides having a sequence complementary to a sequence included within the sequence shown in FIGS. 2A–2E.

This invention also provides a method for determining whether a ligand which is not known to be capable of binding to the $\alpha_{2B}$-adrenergic receptor can bind to the $\alpha_{2B}$-adrenergic receptor.

This invention also concerns an antibody directed to the human $\alpha_{2B}$-adrenergic receptor.

This invention additionally concerns a monoclonal antibody directed to an epitope of the $\alpha_{2B}$-adrenergic receptor present on the surface of a cell and having an amino acid sequence included within the amino acid sequence shown in FIGS. 2A–2E.

This invention concerns a method for detecting the presence of $\alpha_{2B}$-adrenergic receptor on the surface of a cell.

This invention also concerns a method of screening drugs to identify drugs which specifically interact with, and bind to, the $\alpha_{2B}$-adrenergic receptor.

The shaded region represents the $\alpha_{2B}$-adrenergic coding sequence. Arrows indicate overlapping sequencing reactions. Restriction sites are indicated.

FIGS 2A–2E. Nucleotide Sequence and Deduced Amino Acid Sequence of the Human $\alpha_{2B}$-Adrenergic Receptor.

Numbers above the necleotide sequence indicate nucleotide position. DNA sequence of cDNA clone 5A was determined by the chain termination method of Sanger, et al., on denatured double-stranded plasmid templates using Sequenase. Deduced amino acid sequence by translation of a long open reading frame is shown.

FIG. 3A–3B. Comparison of the Primary Structures of the $\alpha_{2B}$-Adrenergic Receptors.

Amino acid sequences (single letter code) are aligned to optimize homology. The putative transmembrane domains are indicated by stars and identified by Roman numerals.

Figure 1:
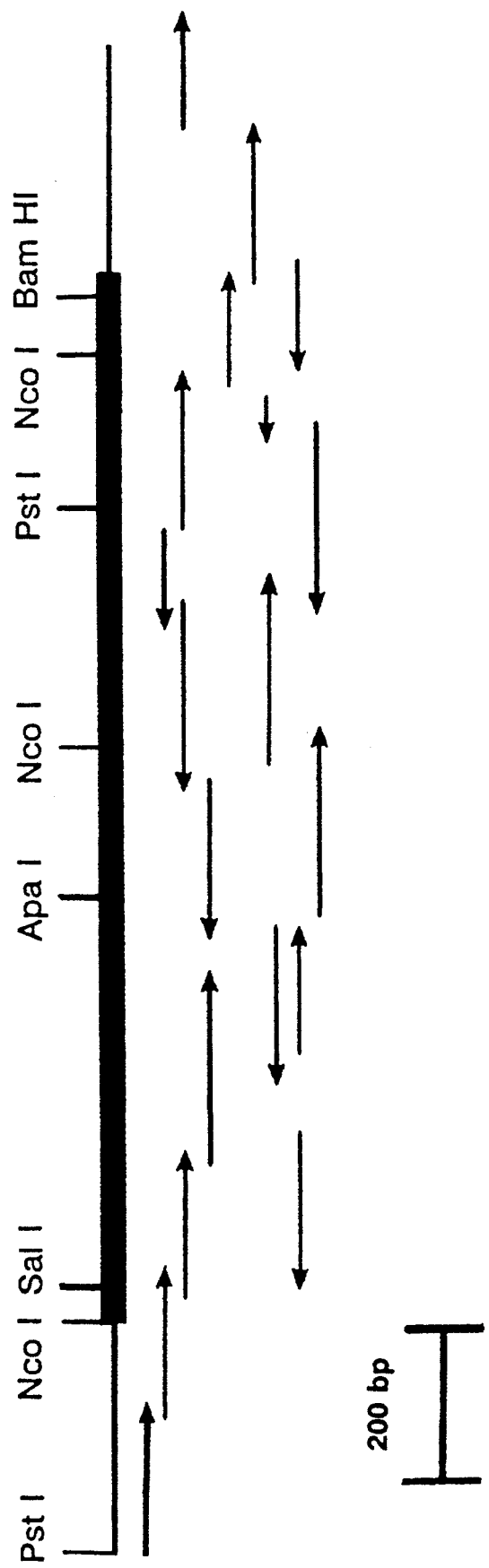
FIG. 1. Restriction Map of pNGC-$\alpha_{2B}$.
Figure 4:
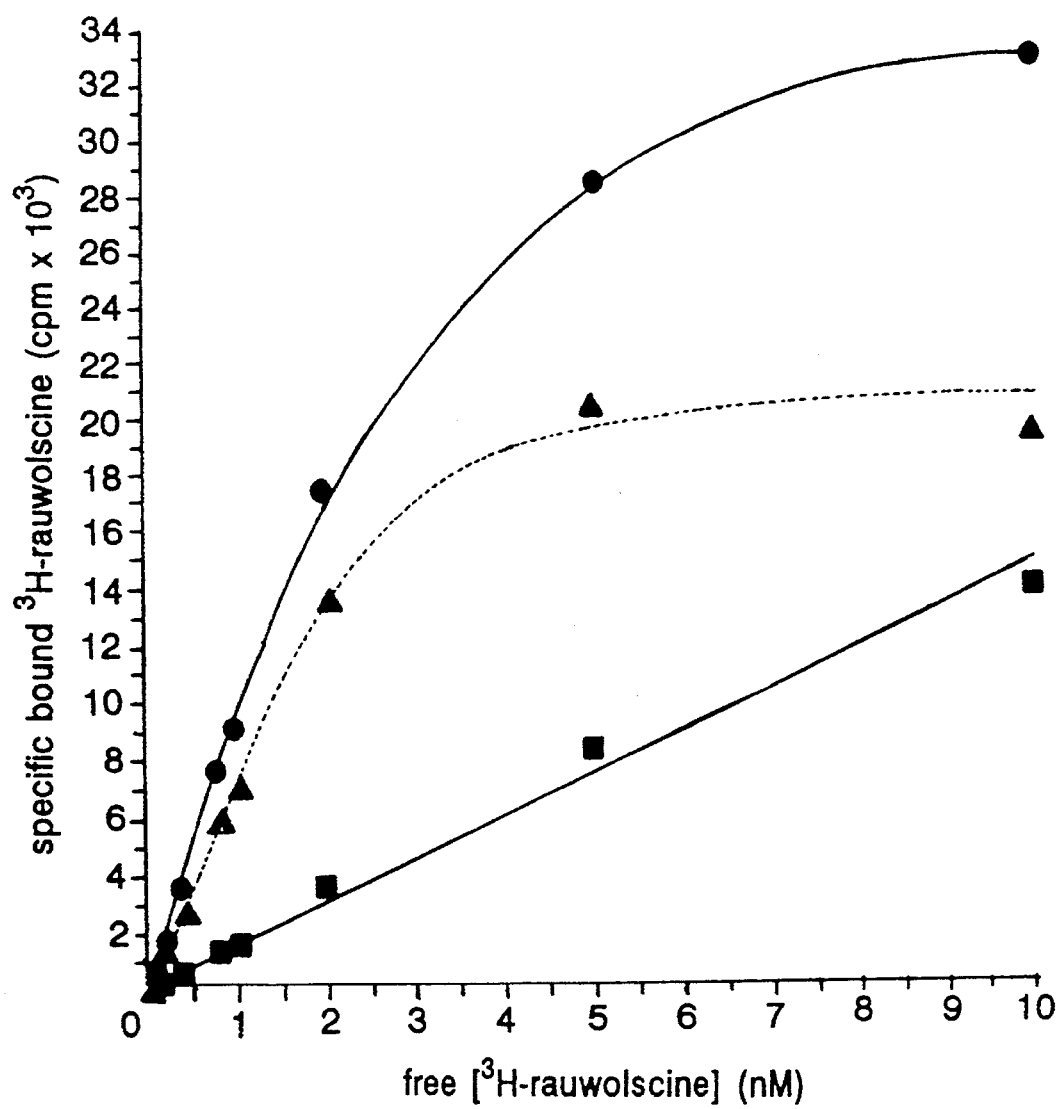

FIG. 4. Saturation Curves for the Bindng of $^3$H-Rauwolscine to Transiently Transfected Cos-7 cells as Shown.

The lower curve represents non-specific binding as defined by $10^{-4}$M(–)norepinephrine. The upper curve represents total binding. The middle curve is the calculated specific binding. For this experiment, $K_D$=1.3 nM; $B_{max}$= 12.8 pmole/mg protein. This dissociation constant is consistent with the designation of NGC-$\alpha_{2B}$ as an $\alpha_{2B}$ receptor.

DETAILED DESCRIPTION OF THE INVENTION

This invention provides an isolated nucleic acid molecule encoding a human $\alpha_{2B}$-adrenergic receptor, for example a DNA molecule or a cDNA molecule.

This invention provides DNA encoding an $\alpha_{2B}$-adrenergic receptor, for example the genomic DNA or cDNA having a coding sequence substantially the same as the coding sequence shown in FIGS. 2A–2E.

This invention provides an isolated protein which is a human $\alpha_{2B}$-adrenergic receptor. An example of such a protein has substantially the same amino acid sequence as the amino acid sequence shown in FIGS. 2A–2E. A means for obtaining isolated human $\alpha_{2B}$-adrenergic receptor is expressing DNA encoding the receptor in a suitable host, such as a bacterial, yeast, or mammalian cell, using methods well known in the art, and recovering the $\alpha_{2B}$-adrenergic receptor after it has been expressed in such a host, again using methods well known in the art.

This invention provides vectors comprising DNA encoding a human $\alpha_{2B}$-adrenergic receptor, and DNA and cDNA having a coding sequence substantially the same as the coding sequence shown in FIGS. 2A–2E. Some examples are a plasmid, such as pUC18, or a virus, or a bacteriophage such as lambda bacteriophage.

One example of a plasmid comprising DNA having a coding sequence substantially the same as the coding sequence shown in FIGS. 2A–2E is the plasmid designated pNGC-$\alpha_{2B}$ described in greater detail hereinafter, and deposited with the American Type Culture Collection in *Escherichia coli* strain MM294 under ATCC Accession No. 68144.

Deposits of *E. coli* strains bearing plasmids pNGC-$\alpha_{2B}$ and pcEXV-$\alpha_{2B}$ and Ltk$^-$ mammalian cells bearing plasmid pNGC-$\alpha_{2B}$, were made, respectively, as ATCC Accession Numbers 68144, 68145, and CRL10275, on Oct. 25, 1989, pursuant to, and in satisfaction of, the Budapest Treaty on the International Recognition of the Deposit of Microorganisms for the Purpose of Patent Procedure and was made with the American Type Culture Collection, 12301 Parklawn Drive, Rockville, Md. 20852. All restrictions imposed by the depositor on the availability to the public of the deposited material will be irrevocably removed upon the granting of the patent. This deposit has been made before pendency of the application for patent and for a term of at least thirty (30) years and at least five (5) years after the most recent request for the furnishing of a sample of the deposit was received by the depository and after the enforceable life of the patent.

This invention further provides a plasmid adapted for expression in a bacterial, yeast, or mammalian cell which comprises DNA encoding the $\alpha_{2B}$-adrenergic receptor, or DNA or cDNA having a coding sequence substantially the same as the coding sequence shown in FIGS. 2A–2E, and the regulatory elements necessary to express such DNA in the bacterial, yeast, or mammalian cell. As regards the latter, those skilled in the art will readily appreciate that numerous plasmids may be constructed utilizing existing plasmids and adapted as appropriate to contain the regulatory elements necessary to express the DNA in the mammalian cell. Numerous mammalian cells may be used including, for example, the mouse fibroblast cell NIH3T3, CHO cells, HeLa cells, etc. One example of a plasmid adapted for the expression of a DNA molecule having a coding sequence substantially the same as the coding sequence shown in FIGS. 2A–2E is the plasmid designated pCEXV-$\alpha_{2B}$ described more fully hereinafter and deposited with the American Type Culture Collection under ATCC Accession No. 68145.

This invention provides expression plasmids used to transfect mammalian cells, for example Ltk$^-$ cells, comprising plasmids adapted for expression in mammalian cells which comprise DNA encoding a human $\alpha_{2B}$-adrenergic receptor, or comprising DNA or cDNA having a coding sequence substantially the same as the coding sequence shown in FIGS. 2A–2E. In one presently preferred embodiment this invention provides an Ltk$^-$ cell transfected with the plasmid designated pcEXV-$\alpha_{2B}$. This cell line is designated L-NGC-$\alpha_{2B}$ and is deposited under ATCC Accession No. CRL 10275. DNA encoding the $\alpha_{2B}$-adrenergic receptor may be otherwise introduced into mammalian cells, e.g., by microinjection, to obtain mammalian cells which comprise DNA, e.g., cDNA or a plasmid, encoding the $\alpha_{2B}$-adrenergic receptor.

This invention further provides a method for determining whether a ligand, such as a known or putative drug, which is not known to be capable of binding to the $\alpha_{2B}$-adrenergic receptor, can bind to the $\alpha_{2B}$-adrenergic receptor. This method comprises contacting a mammalian cell with the ligand under conditions permitting binding of ligands known to bind to the $\alpha_{2B}$-adrenergic receptor, detecting the presence of any of the ligand bound to the $\alpha_{2B}$-adrenergic receptor and thereby determining whether the ligand binds to the $\alpha_{2B}$-adrenergic receptor. An example of a mammalian cell is a mammalian cell comprising a plasmid which comprises a DNA molecule encoding a human $\alpha_{2B}$-adrenergic receptor, or DNA or cDNA molecules having coding sequences substantially the same as the coding sequence shown in FIGS. 2A–2E. Another example of a mammalian cell is an Ltk⁻ cell comprising a plasmid which comprises a DNA molecule encoding a human $\alpha_{2B}$-adrenergic receptor, or DNA or cDNA molecules having coding sequences substantially the same os the coding sequence shown in FIGS. 2A–2E.

This invention still further provides a method of detecting the presence of mRNA coding for the $\alpha_{2B}$-adrenergic receptor in a cell which comprises obtaining total mRNA from the cell, using well known methods, and contacting the mRNA so obtained with the cDNA having a coding sequence substantially the same as the coding sequence encoding the $\alpha_{2B}$-adrenergic receptor shown in FIGS. 2A–2E, under hybridizing conditions, detecting the presence of mRNA hybridized to the cDNA, and thereby detecting the presence of mRNA coding for the $\alpha_{2B}$-adrenergic receptor by the cell.

This invention also provides a DNA probe useful for detecting in a sample nucleic acid encoding the $\alpha_{2B}$-adrenergic receptor. Such a probe comprises a nucleic acid molecule of at least about 15 nucleotides having a sequence complementary to a sequence included within the sequence shown in FIGS. 2A–2E. Such nucleic acid probe technology is well known to those skilled in the art who will readily appreciate that such probes may vary greatly in length and may be labeled with a detectable label, such as a radioisotope or fluorescent dye, to facilitate detection of the probe.

This invention provides an antibody directed to the human $\alpha_{2B}$-adrenergic receptor. Such an antibody may be serum-derived or monoclonal and may be prepared using methods well known in the art. For example, cells such as SR3T3 cells or Ltk⁻ cells may be used as immunogens to raise such an antibody. Alternatively, synthetic peptides may be prepared using commercially available machines and the amino acid sequence shown in FIGS. 2A–2E. As a still further alternative, DNA, such as a cDNA or a fragment thereof, may be cloned and expressed and the resulting polypeptide recovered and used as an immunogen. One example of such an antibody is a monoclonal antibody directed to an epitope of the $\alpha_{2B}$-adrenergic receptor present on the surface of a cell and having an amino acid sequence substantially the same as any part of the amino acid sequence shown in FIGS. 2A–2E.

Still further this invention provides a method of detecting the presence of the $\alpha_{2B}$-adrenergic receptor on the surface of a cell which comprises contacting the cell with a monoclonal or serum-based antibody directed to an exposed epitope on the $\alpha_{2B}$-adrenergic receptor under conditions permitting binding of the antibody to the $\alpha_{2B}$-adrenergic receptor, and detecting the presence of the antibody bound to the cell, and thereby the presence of the $\alpha_{2B}$-adrenergic receptor on the surface of the cell. Such a method is useful in determining whether a given cell is defective relative to the expression of $\alpha_{2B}$-adrenergic receptor on the surface of the cell.

Finally, this invention provides a method of screening drugs to identify drugs which specifically interact with, and bind to, the $\alpha_{2B}$-adrenergic receptor on the surface of a cell. This method comprises contacting a mammalian cell which is expressing $\alpha_{2B}$-adrenergic receptor with a plurality of drugs, known or putative, determining those drugs which bind to the mammalian cell, and thereby identifying drugs which specifically interact with, and bind to, the $\alpha_{2B}$-adrenergic receptor. An example of a mammalian cell is the mammalian cell comprising a plasmid which comprises a DNA molecule encoding a human $\alpha_{2B}$-adrenergic receptor, or DNA or cDNA molecules having coding sequences substantially the same os the coding sequence shown in FIGS. 2A–2E.

Specifically, this invention relates to the first isolation of a human genomic DNA clone encoding an $\alpha_{2B}$-adrenergic receptor by using hybridization to screen clones generated from a human genomic spleen DNA library and expressing an $\alpha_{2B}$-adrenergic binding site in Ltk⁻ cells by transfecting the cells with the DNA from clone NGC-$\alpha_{2B}$. A mammalian cell line expressing an $\alpha_{2B}$-adrenergic receptor at the cell surface has been constructed, as determined by pharmacologic methods, thus establishing the first well-defined, cultured cell line with which to study the human $\alpha_{2B}$-adrenergic receptor.

A genomic DNA molecule such as the molecule of the subject invention, which encodes the human $\alpha_{2B}$-adrenergic receptor, is useful for obtaining genomic DNA, cDNA or mRNA from human, mammalian or other animal sources, or to isolate related cDNA or genomic clones by the screening of cDNA or genomic libraries. The DNA molecule is obtained by insertion of the whole molecule or fragments thereof into suitable vectors, such as plasmids or bacteriophages, wherein it is replicated and harvested following insertion into suitable bacterial host cells, using methods well known in the art. DNA or RNA fragments derived from the isolated DNA molecule are useful as probes for 'in situ' hybridization or in order to locate tissues which express this gene, or for other hybridization assays for the presence of the gene or its mRNA in various biological tissues. In addition, synthesized oligonucleotides complementary to the sequence of the DNA molecule are useful as probes for the $\alpha_{2B}$-adrenergic receptor gene, for its associated mRNA, or for the isolation of related genes by homology screening of genomic or cDNA libraries, or by the use of amplification techniques such as the Polymerase Chain Reaction.

This invention is also useful to obtain the protein, or fragments of the protein, encoded by the isolated DNA molecule encoding the human $\alpha_{2B}$-adrenergic receptor. Transfecting suitable hosts, such as bacterial, yeast or mammalian cells, with the DNA molecule or fragments thereof in suitable expression vectors such as the plasmid pSVL, using methods well known in the art, yields expression of the $\alpha_{2B}$-adrenergic receptor or fragments thereof for direct uses or for experimental study.

Response systems are obtained by coupling the $\alpha_{2B}$-adrenergic receptor encoded by the isolated DNA molecule to an appropriate second messenger response system. These second messenger response systems include, but are not limited to, such systems as phosphoinositide hydrolysis, adenylate cyclase, guanylate cyclase or ion channels. The response system is obtained by transfection of the isolated DNA molecule into a suitable host cell containing the desired second messenger system. Such a host system is isolated from pre-existing cell lines, or is generated by inserting appropriate components of second messenger systems into existing cell lines. Such a transfection system provides a complete response system for investigation or assay of the activity of the $\alpha_{2B}$-adrenergic receptor encoded by the isolated DNA molecule.

This invention is useful to determine whether a ligand, such as a known or putative drug, is capable of binding to and/or activating the $\alpha_{2B}$-adrenergic receptor encoded by the isolated DNA molecule. Transfection of the isolated clone into the cell systems described above provides an assay system for the ability of ligands to bind to and/or to activate the receptor encoded by the isolated DNA molecule. Transfection systems, such as those described above, are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for competitive binding assays. Functional assays of second messenger systems or their sequelae in transfection systems act as assays for binding affinity and efficacy in the the activation of receptor function. Such a tranfection system constitutes a "drug discovery system", useful for the identification of natural or synthetic compounds with potential for drug development that can be further modified or used directly as therapeutic compounds to activate or inhibit the natural functions of the receptor encoded by the isolated DNA molecule. This transfection system is also useful for determining the affinity and efficacy of known drugs at the human $\alpha_{2B}$-adrenergic receptor site.

This invention is useful to isolate the transcriptional regulatory elements from the 5' untranslated region of the isolated clone, and other stability, processing, transcription, translation, and tissue specificity-determining regions from the 3' and 5' untranslated regions of the isolated gene.

This invention is also useful to generate antibodies directed against the $\alpha_{2B}$-adrenergic receptor protein encoded by the isolated DNA molecule. Expression of the protein encoded by the isolated DNA molecule, in transfection systems such as those described above, provides protein or fragments of protein which are further useful to generate monoclonal or polyclonal antibodies against the isolated receptor, using methods well known in the art. These antibodies are useful to detect the presence of the receptor encoded by the isolated DNA molecule, or to inhibit the function of the receptor encoded by the isolated DNA molecule, in living animals, in humans, or in biological tissues or fluids isolated from animals or humans.

This invention identifies an individual receptor subtype protein and tests whether pharmacological compounds interact with it for use in therapeutic treatments. Pharmacological compounds which are directed against specific receptor subtypes will provide effective new therapies with minimal side effects.

In summary, this invention identifies for the first time a human $\alpha_{2B}$-adrenergic receptor protein, its amino acid sequence, and its human gene. The information and experimental tools provided by this discovery will be useful to generate new therapeutic agents, and new therapeutic or diagnostic assays for this new receptor protein, its associated mRNA or its associated genomic DNA.

The invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Isolation of a functional $\alpha_{2B}$-adrenergic receptor human genomic DNA clone.

A human spleen genomic library, in the lambda vector Charon 28 provided by Dr. Jeffrey V. Ravetch (Sloan-Kettering Institute, New York, N.Y.), was screened using the 1.6-kilobase (kb) XbaI-BamHI fragment from the human 5-hydroxytryptamine (5-HT$_{1A}$) receptor gene (also known as G-21), as a probe (A. Fargin, et al., Nature 335: 358–360, 1988). The probe was labeled with $^{32}$P by the method of random priming. (A. P. Feingberg and B. Vogelstein, Anal. Biochem. 137:266. Hybridization was performed at 40° C. in a solution containing 50% formamide, 10% dextran sulfate, 5× SSC (1× SSC is 0.15M sodium chloride, 0.015M sodium citrate) 1× Denhardt's (0.02% polyvinylpyrrolidone, 0.02% Ficoll, and 0.02% bovine serum albumin), and 200 µg/ml of sonicated salmon sperm DNA. The filters were washed at 50° C. in 0.1× SSC containing 0.1% sodium dodecyl sulfate (SDS) and exposed at −70° C. to Kodak XAR film in the presence of an intensifying screen. Lambda phage hybridizing to the probe were plaque purified and DNA was prepared for Southern blot analysis (Maniatis, et al., Molecular Cloning, Cold Spring Harbor, 1982, E. Southern, J. Mol. Biol. 98:503, 1975). For subcloning and further Southern blot analysis DNA was inserted into pUC18 (Pharmacia, Piscataway, N.J.).

DNA Sequencing

Nucleotide sequence analysis was done by the Sanger dideoxy nucleotide chain-termination method (S. Sanger, et al., Proc. Natl. Acad. Sci., 74: 5463–5467, 1977) on denatured double-stranded plasmid templates using Seguenase (U.S. Biochemical Corp., Cleveland, Ohio).

$^3$HRauwolscinc competitive binding to NGC-1 transfected cells (80Ci/mmol;DuPont-NEN)

Membranes were incubated in 5 ml plastic tubes at 22° C. for 30' in solution containing buffer [50 mM Hepes, 5 mM EDTA, 2 mM EGTA, 150 mM NaCl pH 7.6] 1 nM $^3$H-Rauwolscine (80Ci/mmol; DuPont-NEN, Wilmington, DE), 35 µg/ml protein, and drugs. The total reaction volume was 1 ml. The reaction was terminated by dilution with 4 ml of iced buffer and filtration through GF/B filters using a Millipore sample vacuum manifold (Millipore, Bedford, Mass.). Filters were washed 2×4 mls with iced buffer to reduce non-specific binding. Dried filters were transferred to scintillation vials and counted by liquid scintillation spectroscopy using a Beckman LS 1701 LSC. Five ml of Ready-Organic (Beckman Instruments, Fullerton, Calif.) was used as cocktail. Specific binding was 86–88% of total binding.

For $^3$H Yohimbine (88.4 Ci/mmol, DuPont-NEN)

Membranes were incubated in 5 ml plastic tubes for 60' at 22° C. in a solution contain buffer [0.1M TrisCl+10 mM EGTA at pH 7.5], 1 nM $^3$H-Yohimbine, (Dupont-NEN, Wilmington, Del.), 35 µg protein, and drugs. The reaction was terminated by addition of iced buffer. Rapid filtration and subsequent steps were performed as described above.

Saturation Studies

To determine whether the receptor was of the $\alpha_{2B}$ or $\alpha_{2C}$ subtype, saturation analysis was performed using $^3$H-Rauwolscine as a radioligand. The concentration of the 3H-Rauwolscine covered a range between 0.01 and 20 nM. (−) NE (at 0.1 mM) was used to define specific binding. All conditions were as described for $^3$H-Rauwolscine competition studies.

Method for Binding Assays on Stable Cell Line

Subsequent to analysis in transiently transfected cells, NGC-$\alpha_{2B}$ was expressed as a stable transfectant in mouse Ltk$^-$ cells. Further characterization was done as follows: Membranes were incubated in 96 well microtiter plates at 22° C. for 90 minutes in a solution containing 25 mM glycylglycine buffer pH 7.6, 1 nM $^3$H-Rauwolscine (80 Ci/mMol), 60 µg/ml protein and drugs. The total reaction volume was 25 µl. The reaction was terminated by filtration through GF/B filters using a Brandel 48R Cell Harvester (Gaithersbury, Md.). Filters were washed for 5 seconds with iced buffer (50 mM Tris Cl, pH 7.6) to reduce non-specific binding. Dried filters were processed as above. Specific binding was 88% of total binding.

EXPERIMENTAL RESULTS

Isolation of a genomic clone encoding an $\alpha_{2B}$-adrenergic receptor

We have screened a human genomic spleen library with the 1.6 kbXbaI-BamHI restriction fragment derived from the gene for the 5-HT$_{1A}$ receptor. A total of fifteen clones were isolated and were characterized by restriction endonuclease mapping and DNA sequence analysis. By restriction analysis the fifteen clones were categorized into four different families of overlapping clones. By sequence analysis two of the families were identified as previously characterized clones, specifically the $\beta_1$ and the $\beta_2$ adrenergic receptor genes. A third family, designated family 2, was sequenced and a comparison to the human sequences present in Genbank demonstrated that this sequence was novel.

Nucleotide sequence and deduced amino acid sequence of the receptor encoded by family 2

DNA sequence information obtained from clone NGC-$\alpha_{2B}$ of family 2 is shown in FIGS. 2A–2E. An open reading frame extending from an ATG codon at position 1 to a stop codon at position 1463 can encode a protein 487 amino acids in length, having a relative molecular mass (M$_r$) of 53,561. A comparison of this protein sequence with previously characterized neurotransmitter receptors indicates that clone NGC-$\alpha_{2B}$ is a new member of a family of molecules which span the lipid bilayer seven times and couple to guanine nucleotide regulatory proteins (the G protein-coupled receptor family). A variety of structural features which are invariant in this family were present in clone NGC-$\alpha_{2B}$. The greatest homology was found between clone NGC-$\alpha_{2B}$ and the human platelet $\alpha_2$ and the human kidney $\alpha_{2B}$-adrenergic receptors. (B. K. Kobilka, et al., Science 238:650–656, 1987; J. W. Regan, et al., Proc. Natl. Acad. Sci. (USA) 85: 6301–6305, 1988). In both cases, an overall homology of approximately 45% was observed, while the homology within the transmembrane regions alone was approximately 75%.

Receptor expression in transfected mammalian cells

In order to confirm the functional identity of the newly isolated gene we have expressed clone NGC-$\alpha_{2B}$ in a cultured cell line. A DNA fragment containing the entire coding region was subcloned into the expression vector pcEXV-3 (Miller, et al., J. Exp. Med. 164:1478, 1986). The resulting plasmid pcEXV-$\alpha_{2B}$ was transiently introduced into Cos-7 cells using the DEAE-dextran protocol (Cullen, Methods in Enz. 152: 684–704, 1987).

Cos-7 cells were pseudotransfected with pSVL not containing an insert in order to assess endogenous levels of ligand binding. At 1nMor 2nM radioligand, no specific binding was detected. The background was low (80 CPM). Therefore, cos-7 cells provide a useful model for transfection of a putative $\alpha_{2B}$-adrenergic receptor. To facilitate further characterization, the bacterial gene aminoglycoside phosphotransferase contained within the plasmid pGCcos3neo, was cotransfected with the plasmid pcEXV-$\alpha_{2B}$ into Ltk$^{31}$ cells (American Type Culture Collection cell line CCL 1.3, (Rockeville, Md.) using the calcium phosphate technique (kit and protocol obtained from Specialty Media, Inc., Lavellette, N.J.). Clones expressing the aminoglycoside phosphotransferase gene were selected for by the addition of G418 (1mg/ml; Gibco Laboratories, Grand Island, N.Y.) to the culture medium.

Cells transfected with NGC-$\alpha_{2B}$ bound $^3$H-Rauwolscine saturably, specifically, and with high affinity. The binding constants were evaluated by computer-assisted nonlinear regression using Accufit (Lundon Software, Chagrin Falls, Ohio). The equilibrium dissociation constant was 1.39±0.03 nM and the B$_{max}$=12.8±0.05 pm/mg prot. (See FIG. 4) Analysis of the competition data was accomplished using the computer-assisted nonlinear regression program Accucomp. Data are shown in Tables 1 and 2.

TABLE 1

$^3$H-Rauwolscine binding to NGC-1-transfected Cos-7 cells.

| Drug | Concentration | % Inhibition | Selectivity |
|---|---|---|---|
| Isoproterenol | 0.1 mM | 8 | β Adrenergic |
| Oxymetazoline | 1.0 nM | 0 | $\alpha_{2A}$ adrenergic |
| Serotonin | 0.1 mM | 15 | serotoninergic |
| Dopmine | 0.1 mM | 47 | catecholaminergic |
| Prazosin | 1.0 nM | 20 | $\alpha_{2b'}$ $\alpha_{2C}$ |

Competition studies were performed to determine the pharmacological profile of the NGC-$\alpha_{2B}$ clone (see Methods).
Results of the competition studies indicate that the NGC-$\alpha_{2B}$ clone is an $\alpha_{2B}$ or $\alpha_{2C}$ receptor.

TABLE 2

Inhibition of [$^3$H] - Rauwolscine Binding to an $\alpha_{2B}$ - adrenergic receptor in Stable Ltk$^-$ Cells.

| Drug | n | K$_1$ (nM) | n$_H$ (Hill Coefficient) |
|---|---|---|---|
| Rauwolscine | 3 | 0.5 ± 0.1 | 0.88 ± 0.09 |
| Yohimbine | 2 | 2.5 ± 0.4 | 0.84 ± 0.19 |
| Clonidine | 1 | 16 | 1.08 |
| Prazosin | 4 | 32 ± 9 | 0.92 ± 0.09 |
| WB-4101 | 1 | 55 | 1.5 |
| Oxymetazoline | 5 | 283 ± 114 | 0.78 ± 0.15 |
| Corynanthine | 2 | 142 ± 43 | 1.02 ± 0.13 |
| Ketanserin | 3 | 406 ± 74 | 1.21 ± 0.12 |

Competition studies were performed to determine the pharmacological profile of the pNGC-$\alpha_{2B}$ clone stably inserted into Ltk$^-$ cells (see Methods). These data confirm the prediction from transient transfection binding studies that pNGC-$\alpha_{2B}$ encodes an $\alpha_{2B}$ or $\alpha_{2B}$ - related receptor.
K$_i$ values were calculated by the method of Cheng & Prushoff.
n is number of experimental trials.

The high affinity of pNGC-$\alpha_{2B}$ transfected Cos-7 membrane for $^3$H-Rauwolscine indicates that this clone leads to the production of an $\alpha_{2B}$ binding site in its otherwise naive host cells. The drug resistance to oxymetazoline argues against assignment of this clone as an $\alpha_{2B}$ receptor. The inability of drugs active at other receptors ($\beta$, 5-HT) to compete with $^3$H-Rauwolscine for binding is also supportive of the interpretation that pNGC-$\alpha_{2B}$ is an $\alpha_{2B}$ receptor (Tables 1 and 2). The binding constants derived from saturation analysis argue against the assignment of this clone as an $\alpha_{2C}$ receptor. At this time, the available data indicate that this clone is either an $\alpha_{2B}$ receptor or a new subtype closely related to these pharmacologically-defined subtypes.

The deduced protein sequence of the pNGC-$\alpha_{2B}$ clone indicates that applicants have cloned a new member of the gene family encoding G protein-coupled neurotransmitter receptors. To establish further that this clone encodes an $\alpha_{2B}$-adrenergic receptor and to extend the ability to manipulate it, applicants have demonstrated that the introduction of this cDNA into Cos-7 cells or Ltk$^-$ cells causes these cells to bind $^3$H-Rauwolscine.

Discussion

Applicants have cloned and characterized a DNA molecule encoding an $\alpha_2$B-adrenergic receptor. The expression of this DNA clone in Cos-7 cells and Ltk$^-$ cells results in the appearance of this type of receptor on the cell surface.

Binding competition studies of pNGC-$\alpha_{2B}$ transfected Cos-7 or Ltk$^-$ cell membranes with $^3$H-Rauwolscine (Tables 1 and 2) support the interpretation that this clone is an $\alpha_{2B}$ receptor. The inability of isoproterenol (selective for $\beta$-adrenergic receptors) and serotonin (selective for serotonergic receptors) to compete with $^3$H-Rauwolscine for binding support the identification of the pNGC-$\alpha_2$B as an $\alpha$-adrenergic receptor, while its affinity for $^3$H-Rauwolscine (FIGS. 2A–2E) indicates that it is likely to be an $\alpha_2$-adrenergic receptor. Drug resistance to oxymetazoline argues against considering this clone to be an $\alpha_{2A}$ receptor, while binding constants derived from saturation analysis argue against assignment of this clone as an $\alpha_{2C}$ receptor. Thus, the available data indicate that this clone is an $\alpha_{2B}$ receptor or a new, closely related $\alpha_2$ subtype.

What is claimed is:

1. A method for determining whether a compound specifically binds to a human $\alpha_{2b}$ adrenergic receptor which comprises:

a) obtaining a membrane preparation from mammalian cells, said cells 1) comprising an isolated nucleic acid molecule encoding the human $\alpha_{2b}$ adrenergic receptor, and 2) expressing on their cell surface the human $\alpha_{2b}$ adrenergic receptor encoded by the isolated nucleic acid molecule;

b) contacting the compound with the membrane preparation under conditions permitting the binding of the compound to the human $\alpha_{2b}$ adrenergic receptor; and c) detecting the presence of such compound specifically bound to the human $\alpha_{2b}$ adrenergic receptor in the membrane preparation, the presence of such compound specifically bound to the human $\alpha_{2b}$ adrenergic receptor indicating that the compound specifically binds to a human $\alpha_{2b}$ adrenergic receptor.

2. A method of screening drugs to identify drugs that specifically bind to the human $\alpha_{2b}$ adrenergic receptor comprising the method of claim 1.

3. The method of claim 1, wherein the mammalian cell is a non-neuronal cells.

4. The method of claim 3 wherein the mammalian cells are L(tk$^-$) cells.

5. The method of claim 2, wherein the mammalian cell are non-neuronal cells.

* * * * *